(12) United States Patent
Ockert

(10) Patent No.: US 6,503,950 B1
(45) Date of Patent: Jan. 7, 2003

(54) TRIPLE DRUG THERAPY FOR THE TREATMENT OF NARCOTIC AND ALCOHOL WITHDRAWAL SYMPTOMS

(76) Inventor: David M. Ockert, 145 E. 32nd St., Sixth Floor, New York, NY (US) 10016

(*) Notice: Subject to any disclaimer, the term of this patent is extended or adjusted under 35 U.S.C. 154(b) by 0 days.

(21) Appl. No.: 09/634,555

(22) Filed: Aug. 8, 2000

Related U.S. Application Data

(60) Provisional application No. 60/150,249, filed on Aug. 23, 1999.

(51) Int. Cl.$^7$ ............... A61K 31/165; A61K 31/5513; A61K 31/4168; A61K 31/155; A61K 31/195; A61K 31/192; A61K 31/438; A61K 31/495; A61K 31/522; A61K 31/4458; A61K 31/137; A61K 31/421

(52) U.S. Cl. ............ 514/618; 514/221; 514/401; 514/617; 514/567; 514/811; 514/634; 514/278; 514/225.04; 514/263; 514/317; 514/654; 514/376; 514/377; 514/653

(58) Field of Search ............ 514/618, 392, 514/221, 654, 810, 811, 812, 401, 617, 567, 634, 278, 225.04, 263, 317, 376, 377, 653; 424/464

(56) References Cited

U.S. PATENT DOCUMENTS

| | | | |
|---|---|---|---|
| 4,829,070 A | 5/1989 | Bodor | 514/307 |
| 5,288,497 A | 2/1994 | Stanley et al. | 424/440 |
| 5,474,783 A | 12/1995 | Miranda et al. | 424/448 |
| 5,668,117 A | 9/1997 | Shapiro | 514/55 |
| 5,855,908 A | 1/1999 | Stanley et al. | 424/440 |

OTHER PUBLICATIONS

Stedman's Medical Dictionary. 25$^{th}$ Ed., 1990, pp. 745, 857.*
Mondavio et al. Clonidine As A Preventative Treatment Of Alcohol Withdrawal, Nov. 1, 1989, Minerva Medica, vol. 80, pp. 1233–1235.*
Guthrie S. K., The treatment of alcohol withdrawal, Pharmacotherapy, 1989, 9th Ed., vol. 3, pp. 131–143. AN 1989–36764.*
Riley et al., Drug Facts and Comparisions, 1999, pp. 232f and 261g.*
Schmidt et al., antihypertensive agents, Harper's Handbook of Therapeutic Pharmacology, 1981, p. 227.*
Laffont F., Clinical assessment of modafinil, Drugs Today, 1996, vol. 32, pp. 35–44. AN 1997:75024.*

* cited by examiner

Primary Examiner—Edward J. Webman
Assistant Examiner—Helen Nguyen
(74) Attorney, Agent, or Firm—Price, Heneveld, Cooper, DeWitt & Litton

(57) ABSTRACT

A triple drug, pharmaceutical kit, composition, and method of treatment containing a combination of effective amounts of at least one anxiolytic agent, at least one centrally acting alpha antiadrenergic agent, and at least one central nervous system stimulant for the reduction or prevention of alcohol and narcotic withdrawal side effects of dizziness, drowsiness, depression, lethargy, orthostatic hypotension, weakness in the extremities, and difficulty in being mobile, caused by therapeutic agents utilized for the treatment of alcohol or narcotic withdrawal symptoms in patients overcoming alcohol or narcotic addiction.

63 Claims, 1 Drawing Sheet

TRIPLE DRUG THERAPY FOR THE TREATMENT OF NARCOTIC AND ALCOHOL WITHDRAWAL SYMPTOMS

The present application claims priority to Provisional Application Serial No. 60/150,249 filed on Aug. 23, 1999.

BACKGROUND OF THE INVENTION

1. Field of the Invention

The present invention relates to the treatment of alcohol and narcotic withdrawal symptoms associated with alcohol and narcotic addiction.

2. Description of the Related Art/Background Information

Alcohol and narcotic withdrawal symptoms associated with patient populations undergoing drug abuse treatment has become an important concern to those patients and their families as well as treating health care personnel. Due to alcohol and narcotic abuse, use, and the high rate of relapse to regular use, the management of withdrawal side effects is becoming increasingly important for the long-term rehabilitation of patients overcoming drug abuse addiction. Current treatment modalities for drug abuse can create or potentiate side effects from those medications used to treat alcohol or narcotic withdrawal. Frequently encountered side effects include depression, dizziness, orthostatic hypotension, drowsiness, lethargy, difficulty in being mobile, and weakness in the extremities. Such negative side effects prolong patient therapy or interfere with detoxification procedures, which leads to further use, abuse, and relapses to regular use, requiring subsequent detoxification. treatment episodes.

The prior art teaches the use of benzodiazepines separately for the treatment of anxiety caused by a variety of conditions, including withdrawal. For example, the drug monograph for benzodiazepines listed within the *Drug Facts and Comparisons*, 1999 ed., Wolters Kulwar Co. 1998, p. 1600–03, indicates that such agents, through interaction with gamma-aminobutyrate (GABA) and $BZ_1$ and $BZ_2$ receptors in the human body, create a calming effect and subsequent reduction or prevention of anxiety. The prior art also teaches the use of azaspirodecanediones, such as buspirone, as an anxiolytic agent, because of their calming effect caused by interaction with $5\text{-}HT_1A$ and GABA receptors in the human body. Id. Finally, the prior art also teaches the use of piperazine derivatives, such as hydroxyzine, to create a calming effect in the human body through interaction with spasmogenic receptors for serotonin, acetylcholine and histamine. Id. at 1604–07. Yet, all these anxiolytic agents, due to their drug chemistry, cause the side effects of drowsiness, depression, lethargy, and difficulty in being mobile in patients undergoing drug abuse treatment. Such negative side effects frequently increase the need to treat such patients in an in-patient only setting to prevent the risk of injury.

The individual use of centrally acting alpha antiadrenergic agents to reduce central and peripheral nerve agitation and increased blood pressure associated with narcotic and alcohol withdrawal has been taught by the prior art. The use of such agents can decrease central and peripheral nerve agitation, yet, frequently cause depression, dizziness, drowsiness, lethargy, orthostatic hypotension, and weakness in the extremities. *Drug Facts and Comparisons.* 1999 ed., 1998, p. 967–68, 1444–45. In addition, when a centrally acting alpha antiadrenergic agent, such as clonidine, is added to an existing drug treatment regimen, already containing an anxiolytic agent, an additive effect for dizziness, drowsiness, depression, lethargy, weakness in the extremities, orthostatic hypotension, and difficulty in being mobile occurs. *Drug Facts and Comparisons.* 1999 ed., 1998, p. 967–68, 1444–45. This further exacerbates the need for in-patient care due to the increased risk of injury to patients and liability to healthcare personnel treating such patients.

U.S. Pat. No. 5,668,117 to Shapiro, discloses a method of treating neurological diseases and etiology by utilizing carbonyl-trapping agents in combination with previously known medicaments. Shapiro discloses the ability of combining a carbonyl-trapping agent with either a benzodiazepine or a centrally acting alpha antiadrenergic agent.

Prior art U.S. Pat. No. 4,829,070 to Boder, discloses the use of a redox carrier system for the site-specific delivery of a centrally acting therapeutic agent to the brain. Boder discloses the ability of attaching a centrally acting alpha antiadrenergic agent or benzodiazepine to the redox carrier system and delivering those agents to the brain.

U.S. Pat. No. 5,855,908 to Stanley, discloses a non-dissolvable dosage form for use in the transdermal delivery of a drug to a patient which includes clonidine or a benzodiazepine agent, such as lorazepam, to be carried by such a transdermal system.

U.S. Pat. No. 5,474,783 to Miranda, discloses a pressure sensitive adhesive transdermal drug delivery system which includes an adhesive carrier that holds a therapeutic agent such as a centrally acting alpha antiadrenergic agent or anxiolytic agent, or central nervous system stimulant agent to be delivered to the human body.

Prior art clinical addiction treatment literature includes many descriptions of patients having an incipient form of a disease, such as alcohol or narcotic addiction, who show the recognized symptoms of the disease, such as withdrawal. It should be understood by those skilled in the art that a narcotic is a drug that dulls the senses, relieves pain, and produces sleep, such as an opiate or benzodiazepine. Treatment options for side effects associated with conventional drug therapies used to treat the established clinical withdrawal side effects of alcohol and narcotic addiction have not been reported.

Prior art clinical neurology literature includes many descriptions of patients having increased drowsiness, dizziness, depression, weakness in the extremities, lethargy, orthostatic hypotension, and difficulty in being mobile associated with treatments utilizing anxiolytic agents and centrally acting alpha antiadrenergic agents for the reduction or prevention of alcohol or narcotic withdrawal symptoms such as anxiety, central and peripheral nerve agitation, and hypertension associated with alcohol and narcotic addiction. Dunagan, W. and Ridner, M., *Manual of Medical Therapeutics*, 26th ed., Boston, Little, Brown, 1989, p. 6–7, 474–75. Clinical cardiology literature in the prior art includes many descriptions of patients experiencing orthostatic hypotension and other side effects associated with centrally acting alpha antiadrenergic agents utilized to treat hypertension and central and peripheral nerve agitation experienced during alcohol or narcotic withdrawal management. Woodley, M. and Whalen A., *Manual of Medical Therapeutics*, 27th ed., Boston, Little, Brown, 1992, p. 64–75.

Due to the lack of clinical literature and study of withdrawal side effect management, such as depression, dizziness, drowsiness, weakness in the extremities, lethargy, orthostatic hypotension, and difficulty in being mobile associated with the use of centrally acting alpha antiadrenergic agents and anxiolytic agents, many patients do not initiate or continue an alcohol or narcotic abuse treatment program.

Further, due to the increased orthostatic hypotension associated with the use of centrally acting alpha antiadrenergic agents, an increased risk of syncope and injurious fall to patients undergoing abuse treatment has been frequently observed. This increased risk further prompts the need to treat such patients in an in-patient only setting to decrease the risk of liability for health care personnel providing treatment. Yet, in doing so, healthcare costs are substantially increased.

SUMMARY OF THE INVENTION

A pharmaceutical kit, composition, and method of treatment regimen for alcohol and narcotic withdrawal side effects of therapeutic agents used to treat alcohol or narcotic withdrawal symptoms has been discovered, utilizing a centrally acting alpha antiadrenergic agent, a central nervous system stimulant agent (CNS), and an anxiolytic agent in combination. The present invention reduces or prevents the side effects of depression, dizziness, drowsiness, lethargy, weakness in the extremities, difficulty in being mobile, and orthostatic hypotension associated with therapeutic agents used to treat alcohol and narcotic withdrawal without compromising the positive clinical effects of those same therapeutic agents.

By reducing or preventing these side effects, the present invention also decreases the risk of injury to patients and liability to healthcare personnel treating such patient populations. Further, by reducing the risk to patient and health personnel alike, the present invention increases the opportunity for out-patient treatment settings, which in turn decreases overall healthcare costs. Finally, by minimizing side effects to patients undergoing alcohol or narcotic abuse treatments with the present invention, incidences of relapse to regular use during a detoxification treatment episode are reduced or prevented.

The present invention can be embodied in a variety of pharmaceutically acceptable immediate and sustained release dosage forms and can be delivered to the human body via a variety of medically and pharmaceutically acceptable administration routes.

These and other features, advantages and objects of the present invention will be further understood and appreciated by those skilled in the art by reference to the following specification, claims and appended drawings. A more detailed description of the present invention shall be discussed further below.

DETAILED DESCRIPTION OF THE PRESENT INVENTION

Figure 1:
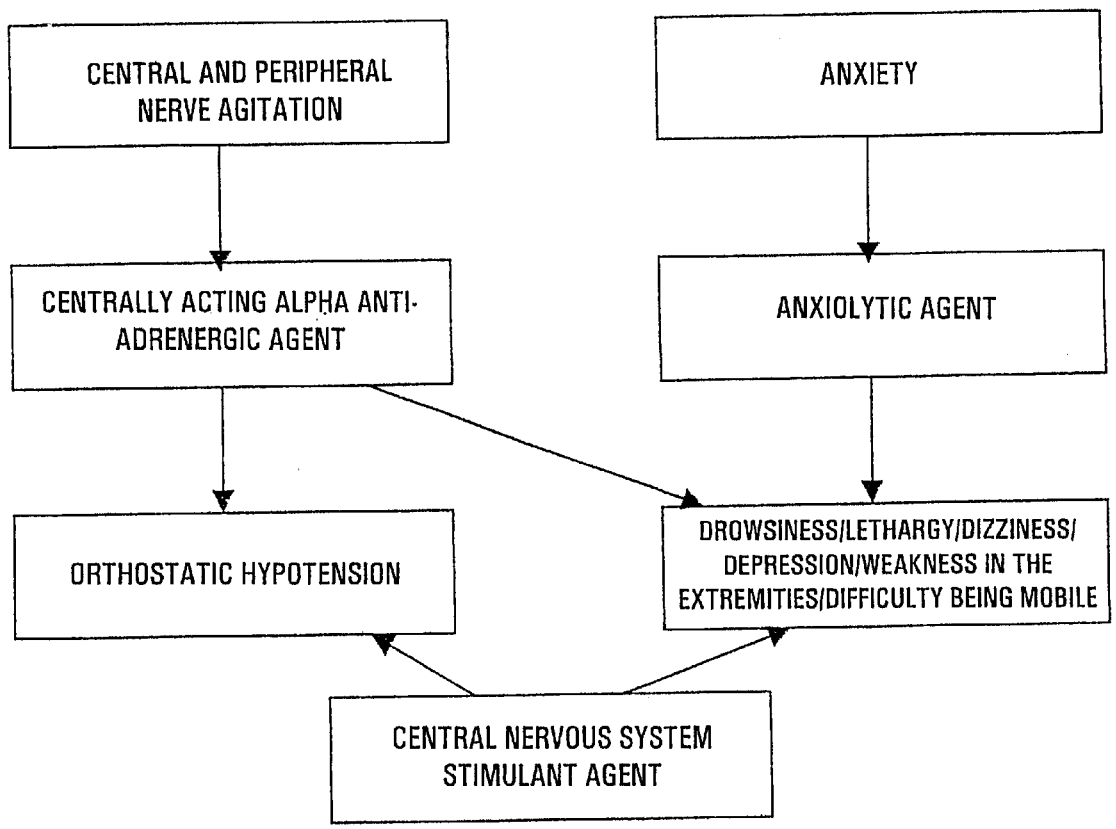
FIG. 1 is a flow diagram indicating the prevention or reduction of side effects associated with therapeutic agents used to treat alcohol or narcotic withdrawal symptoms of alcohol and narcotic addiction, through the use of the triple drug kit, composition, and method of treatment of the present invention, without compromising the positive clinical effects of those same therapeutic agents.

The preferred embodiment is comprised of a pharmaceutical kit, composition, and method of treatment regimen containing a combination of effective amounts of an anxiolytic agent, centrally acting alpha antiadrenergic agent, and central nervous system (CNS) stimulant agent for the reduction or prevention of the withdrawal side effects of drowsiness, dizziness, depression, weakness in the extremities, lethargy, orthostatic hypotension, and difficulty in being mobile associated with therapeutic agents utilized to treat alcohol and narcotic withdrawal symptoms of alcohol and narcotic addiction.

The anxiolytic agent utilized in the preferred embodiment consists essentially of an effective amount of a benzodiazepine, azaspirodecanedione, or piperazine derivative. Suitable benzodiazepine agents include, but are not limited to, diazepam, alprazolam, chlordiazepoxide, clonazepam, clorazepate, halazepam, lorpam, oxazepam, derivatives thereof, and pharmaceutically acceptable salts thereof. Suitable azaspirodecanedione agents include, but are not limited to, buspirone, derivatives thereof, and pharmaceutically acceptable salts thereof. Suitable piperazine derivatives include, but are not limited to, hydroxyzine pamoate and hydroxyzine hydrochloride, derivatives thereof, and pharmaceutically acceptable salts thereof.

The preferred anxiolytic agent for the management of alcohol withdrawal symptoms is about 50 to 60 mg of chlordiazepoxide given to a human being about every 6–8 hours around the clock initially, and gradually tapered by about 10 mg per day for a period of about 5–14 days to reduce or prevent the withdrawal symptom of anxiety and seizure and to prevent patient addiction to chlordiazepoxide, as a substitute for alcohol.

Those skilled in the art will appreciate and will be able to adjust the dose, dosing interval, and dosing length/treatment period of the anxiolytic agent of the preferred embodiment in the treatment of alcohol withdrawal symptoms, based upon the clinical response and therapeutic value required to reduce or prevent withdrawal anxiety and seizure for a particular patient undergoing alcohol abuse treatment. One skilled in the art will appreciate and be able to adjust the dose, dosing interval, and length of treatment with the anxiolytic agent of the preferred embodiment based upon the liver and kidney function of the patient and the amount of CNS stimulant used within the preferred embodiment.

The preferred anxiolytic agent for the management of narcotic withdrawal symptoms is about 0.25 to 10 mg of lorazepam given to a human being about every 4–10 hours, preferably about every 6–10 hours, and most preferably about every 6–8 hours during the day and about every 3–4 hours at night, up to a typical maximum dose of about 10 mg per day or greater, most preferably a maximum of about 7 mg per day. Total daily dosing will occur over about 5–14 days, with initial doses maximizing at about 7–10 mg per day and tapering thereafter by about 1 mg or greater each day of treatment until dosing is completed within a period of about 5–14 days.

Those skilled in the art will appreciate and be able to adjust the dose, dosing interval, and dosing length/treatment period of the anxiolytic agent of the preferred embodiment in the treatment of narcotic withdrawal symptoms based upon the clinical response and therapeutic value required to reduce or prevent withdrawal anxiety for a patient, liver and kidney function of the patient, and the amount of CNS stimulant used within the preferred embodiment.

As the dose of the CNS stimulant is increased or the interval of dosing is decreased, the anxiolytic agent dose can be decreased and dosing interval increased. In addition, it should be understood by those skilled in the art that the dose of the CNS stimulant can be increased to achieve therapeutic efficacy in managing side effect outcomes of the anxiolytic agent of the preferred embodiment as the dose of the anxiolytic agent is increased to treat the withdrawal symptomology of a particular patient undergoing alcohol or narcotic abuse treatment.

The centrally acting alpha antiadrenergic agent of the preferred embodiment consists essentially of an effective amount of methyldopa, clonidine, guanfacine, guanabenz, lofexidine, derivatives thereof, or pharmaceutically acceptable salts thereof. It is recognized that lofexidine is not currently approved for use in the U.S. by the FDA, but is approved for use in Europe. The preferred centrally acting alpha antiadrenergic agent for treatment of alcohol and narcotic withdrawal side effects is about 0.05–0.7 mg of clonidine given to a human being about every 6–8 hours for a period of about 5–14 days. Use of such agents reduces or prevents central and peripheral nerve agitation associated with alcohol and narcotic withdrawal. Typical maximal dosages of clonidine can be about 2 mg per day or higher depending upon the particular patient response required for the particular detoxification setting, liver and kidney function of the patient, and the dose and dosing interval of the central nervous system stimulant agent of the preferred embodiment during that patient's alcohol or narcotic abuse treatment course.

As the dose of the CNS stimulant is increased or the dosing interval is decreased, the centrally acting alpha antiadrenergic agent dose can be decreased and dosing interval increased. In addition, it should be understood by those skilled in the art that the dose of the CNS stimulant can be increased to achieve therapeutic efficacy in managing side effect outcomes of the centrally acting alpha antiadrenergic agent of the preferred embodiment as the dose of the centrally acting alpha antiadrenergic agent is increased to treat the withdrawal symptomology of a particular patient undergoing abuse treatment. Those skilled in the art will appreciate and will be able to adjust the dose, dosing interval, and dosing length treatment period of the centrally acting alpha antiadrenergic agent of the preferred embodiment based upon the factors listed above, to reduce or prevent central and peripheral nerve agitation for a particular patient undergoing alcohol or narcotic detoxification treatment.

The central nervous system stimulant agent of the preferred embodiment consists essentially of an effective amount of an amphetamine, such as amphetamine sulfate, dextroamphetamine sulfate, methamphetamine hydrochloride, combinations of amphetamines, derivatives and pharmaceutically salts thereof; pemoline, derivatives and pharmaceutically acceptable salts thereof; methylphenidate, derivatives and pharmaceutically acceptable salts thereof; caffeine, derivatives and pharmaceutically acceptable salts thereof; and centrally acting alpha-1 agonists such as modafinil, epinephrine, norepinephrine, phenylephrine, derivatives thereof and pharmaceutically acceptable salts thereof to reduce or prevent dizziness, depression, difficulty in being mobile, drowsiness, lethargy, weakness in the extremities, and orthostatic hypotension associated with anxiolytic and centrally acting alpha antiadrenergic agents utilized to treat alcohol and narcotic withdrawal symptomology.

The preferred central nervous system stimulant agent for the treatment of side effects associated with therapeutic agents used to treat alcohol and narcotic withdrawal symptoms is about 1–20 mg dextroamphetamine sulfate in an immediate release dosage form given to a human being about every 4–8 hours, preferably about every 4–6 hours at regular spaced intervals during the day and up to about 5 mg as a rescue dose during the night if needed for a period of about 5–14 days. In a controlled release dosage form, the central nervous system stimulant, dextroamphetamine sulfate, is dosed as 1–20 mg given to a human being about every 12 hours or once daily without a rescue dose given during the night, for a total treatment period of about 5–14 days.

In an alternative embodiment, for those patients requiring a non-amphetamine based central nervous system stimulant agent or those who cannot receive additional or increased amphetamine doses due to cardiovascular risk concerns, a centrally acting alpha-1 agonist, such as modafinil, can be used as a substitute or adjunct for an amphetamine(s), as the central nervous system stimulant agent of the preferred embodiment.

Centrally acting alpha-1 agonists such as modafinil (Provigil®) act postsynaptically at alpha-1 adrenergic receptors and may also bind to dopamine carriers to increase stimulation and mental alertness within the human body usually without altering the body's blood pressure and heart rate excessively like that of amphetamines. Further, centrally acting alpha-1 agonists do not decrease stage 2 and REM sleep like amphetamines, and thus offer a treatment alternative for the practitioner when choosing a central nervous stimulant agent of the preferred embodiment.

In the alternative embodiment, the preferred central nervous system stimulant agent for the treatment of side effects associated with therapeutic agents used to treat alcohol and narcotic withdrawal symptomology is about 50–400 mg, preferably about 100–300 mg, and most preferably about 200 mg or higher per day of modafinil administered to a human being every 12 hours, more preferably once daily in the morning, for a period of 5–14 days.

It should be understood by those skilled in the art that the preferred embodiment of the present invention can utilize any of the central nervous system stimulant agents alone or in combination with one another as the central nervous system stimulant agent component of the preferred embodiment. For example, a practitioner administering the preferred embodiment containing an amphetamine initially as the central nervous system stimulant agent could add modafinil as an adjunct central nervous system stimulant to a particular patient's drug treatment therapy where use of an additional amphetamine would not be desirable and dosing of the current amphetamine could not be increased due to blood pressure and heart rate considerations.

Those skilled in the art can appreciate and would be able to adjust the dose, dosing interval, and dosing length treatment period of the central nervous system stimulant of the preferred embodiment based upon the clinical and therapeutic response desired for a particular patient undergoing alcohol or narcotic abuse treatment, liver and kidney function of that patient, as well as drug interactions between the central nervous system stimulant agent and other components of the preferred embodiment.

All of the components of the preferred embodiment can be used separately, but administered contemporaneously and can be given via a singular pharmaceutically acceptable dosage form for each component or combination of all the components as an immediate release or controlled release dosage form. Contemporaneously means the three agents are administered separately over time, but have a combined effect together after their individual administrations. Suitable pharmaceutical dosage forms for the preferred embodiment include, but are not limited to, tablets, capsules, caplets, dose-paks, solutions, syrups, suppositories, transdermal applications, creams, lotions, emulsions, powders and the like. Preferred dosage forms for the present invention include tablets, caplets, capsules, dose-paks, solutions, and transdermal applications with a tablet, caplet, or capsule being the most preferred.

The triple drug therapeutic composition, kit, and method of treatment of the preferred embodiment can be administered to the human body via a variety of medically and pharmaceutically acceptable administration routes. Those routes include, but are not limited to, the oral, rectal, intravenous, intradermal, subcutaneous, cutaneous, intramuscular, buccal, transdermal, and other pharmaceutically and medically acceptable routes of administration for the human body. Preferred routes of administration for the preferred embodiment are the oral, rectal, intravenous and intramuscular routes, with the oral route being most preferred.

By combining the pharmaceutical medicaments of the preferred embodiment in a kit, composition, and method of treatment regimen, the preferred embodiment achieves far superior alcohol and narcotic withdrawal side effect management results than can be achieved with current conventional prior art treatment modalities. Current treatment modalities for alcohol and narcotic withdrawal symptoms utilize anxiolytic agents and centrally acting alpha antiadrenergic agents to reduce or prevent anxiety and central and peripheral nerve agitation for patients undergoing alcohol or narcotic abuse treatment. Current treatment modalities do not, however, prevent or reduce the negative withdrawal side effects of drowsiness, dizziness, lethargy, depression, difficulty in being mobile, weakness in the extremities, and orthostatic hypotension caused by anxiolytic agents and centrally acting alpha antiadrenergic agents used to treat alcohol or narcotic withdrawal symptoms.

As a result, most patients become non- or mal-compliant in taking such medications because of these negative side effect outcomes which, in turn, can cause an increase in the incidence of relapse for alcohol or narcotic abuse requiring further treatment. In addition, these negative side effects associated with the use of anxiolytic and centrally acting alpha antiadrenergic agents place patients at a greater risk of injury, and health personnel at a greater risk of liability prompting the increased use of in-patient treatment settings only. Such increased risks and liability further increase healthcare costs.

Although not being bound to any particular theory, it is believed that the preferred embodiment reduces or prevents the negative withdrawal side effects of drowsiness, dizziness, depression, difficulty in being mobile, lethargy, weakness in the extremities, and orthostatic hypotension associated with the use of centrally acting alpha antiadrenergic agents and anxiolytic agents used to treat alcohol and narcotic withdrawal symptoms through the use of a central nervous system stimulant agent or agents to stimulate the release of norepinephine from central nonadrenergic neurons, epinephrine from adrenergic neurons, and the release of dopamine from the mesolimbic system of the human central nervous system to counteract the negative withdrawal side effects of agents used to treat alcohol or narcotic withdrawal symptomology.

Thus, patients become more compliant with their therapy by experiencing fewer of the negative withdrawal side effects caused by anxiolytic and centrally acting alpha antiadrenergic agents, thereby decreasing the incidence of relapse and the need for additional cycles of abuse treatment. Further, by increased central nervous system stimulation, patients are at a reduced risk of syncope allowing for the increased use of out-patient treatment settings for these individuals, thereby decreasing the overall cost of health care.

The above description is considered that of the preferred embodiments only. Modifications of the invention will occur to those skilled in the art and to those who make or use the invention. Therefore, it is. understood that the embodiments shown in the drawings and described above are merely for illustrative purposes and not intended to limit the scope of the invention, which is defined by the following claims as interpreted according to the principles of patent law, including the Doctrine of Equivalents.

The invention claimed is:

1. A pharmaceutical kit for treatment of alcohol withdrawal symptoms comprising the following three separate ingredients, combined in a kit:
   at least one anxiolytic agent;
   at least one centrally acting alpha antiadrenergic agent; and
   at least one central nervous system stimulant agent.

2. The pharmaceutical kit of claim 1, wherein said kit contains an effective amount of said anxiolytic agent to reduce anxiety and seizure, an effective amount of said centrally acting alpha antiadrenergic agent to reduce or prevent central and peripheral nerve agitation, and an effective amount of said central nervous system stimulant agent to reduce or prevent negative withdrawal side effects associated with alcohol withdrawal treatment.

3. The pharmaceutical kit of claim 2, wherein said anxiolytic agent comprises at least one member selected from the group consisting of a benzodiazepine, azaspirodecanedione, piperazine derivative, derivatives thereof, and pharmaceutically acceptable salts thereof.

4. The pharmaceutical kit of claim 3, wherein said benzodiazepine comprises at least one member selected from the group consisting of diazepam, alprazolam, clonazepam, clorazepate, chlordiazepoxide, halazepam, lorazepam, oxazepam, derivatives thereof, and pharmaceutically acceptable salts thereof.

5. The pharmaceutical kit of claim 4, wherein said benzodiazepine is chlordiazepoxide.

6. The pharmaceutical kit of claim 5, wherein said effective amount of said chlordiazepoxide is about 50–60 mg per dose.

7. The pharmaceutical kit of claim 3, wherein said benzodiazepine is lorazepam and said effective amount of said lorazepam is about 0.25–10 mg per dose.

8. The pharmaceutical kit of claim 2, wherein said centrally acting alpha antiadrenergic agent comprises of at least one member selected from the group consisting of methyldopa, clonidine, guanfacine, lofexidine, guanabenz, derivatives thereof and pharmaceutically acceptable salts thereof.

9. The pharmaceutical kit of claim 8, wherein said centrally acting alpha antiadrenergic agent is clonidine and said effective amount of said clonidine is about 0.05–0.7 mg per dose.

10. The pharmaceutical kit of claim 2, wherein said central nervous system stimulant agent comprises of at least one member selected from the group consisting of an amphetamine, methylphenidate, pemoline, caffeine, centrally acting alpha-1 agonist, derivatives thereof, and pharmaceutically acceptable salts thereof.

11. The pharmaceutical kit of claim 10, wherein said central nervous system stimulant is dextroamphetamine sulfate and said effective amount of said dextroamphetamine sulfate is about 1–20 mg per dose.

12. The pharmaceutical kit of claim 11, wherein said dextroamphetamine sulfate is in a sustained release form.

13. The pharmaceutical kit of claim 10, wherein said central nervous system stimulant agent is modafinil and said effective amount of said modafinil is about 50–400 mg or greater per dose.

14. The pharmaceutical kit of claim 13, wherein said effective amount of said modafinil is about 200 mg per dose.

15. The pharmaceutical kit of claim 2, wherein said anxiolytic agent comprises at least one member selected from the group consisting of a benzodiazepine, azaspirodecanedione, piperazine derivative, derivatives thereof, and pharmaceutically acceptable salts thereof; wherein said centrally acting alpha antiadrenergic agent comprises at least one member selected from the group consisting of methyl dopa, clonidine, guanfacine, lofexidine, guanabenz, derivatives thereof and pharmaceutically acceptable salts thereof; wherein said central nervous system stimulant agent comprises of at least one member selected from the group consisting of an amphetamine, methylphenidate, pemoline, caffeine, centrally acting alpha-1 agonist, derivatives thereof and pharmaceutically acceptable salts thereof; and further wherein said benzodiazepine comprises of at least one member selected from the group consisting of diazepam, alprazolam, clonazepam, chlorazepate, chlordiazepoxide, halazopam, lorazepam, oxazepam, derivatives thereof, and pharmaceutically acceptable salts thereof.

16. The pharmaceutical kit of claim 15, wherein said combination comprises about 0.25–10 mg of lorazepam, about 0.05–0.7 mg of clonidine, and about 1–20 mg of dextroamphetamine sulfate per dose of said combination.

17. The pharmaceutical kit of claim 15, wherein said combination comprises about 50–60 mg of chlordiazepoxide, about 0.05–0.7 mg of clonidine, and about 1–20 mg of dextroamphetamine sulfate per dose of said combination.

18. The pharmaceutical kit of claim 15, wherein said combination comprises: about 0.25–10 mg of said lorazepam, about 0.05–0.7 mg of said clonidine, and about 50–400 mg or greater of modafinil per dose of said combination.

19. The pharmaceutical kit of claim 15 wherein said combination comprises about 50–60 mg of said chlordiazepoxide, about 0.05–0.7 mg of clonidine, and about 50–400 mg or greater of modafinil per dose of said combination.

20. The pharmaceutical kit of claim 15, wherein said combination comprises about 0.25–10 mg of lorazepam, about 0.05–0.7 mg of clonidine, about 50–400 mg or greater of said modafinil, and about 1–20 mg of dextroamphetamine sulfate per dose of said combination.

21. The pharmaceutical kit of claim 15, wherein said combination comprises about 50–60 mg chlordiazepoxide, about 0.05–0.7 mg of clonidine, about 1–20 mg dextroamphetamine sulfate, and about 50–400 mg or greater of modafinil per dose of said combination.

22. A pharmaceutical composition for the treatment of alcohol and narcotic withdrawal symptoms comprising a combination of at least one anxiolytic agent; at least one centrally acting alpha antiadrenergic agent; and at least one central nervous system stimulant agent.

23. The pharmaceutical composition of claim 22, wherein said composition comprises of an effective amount of said anxiolytic agent to reduce or prevent anxiety and seizure, an effective amount of said centrally acting alpha antiadrenergic age to reduce or prevent central and peripheral nerve agitation, and an effective amount of said central nervous system stimulant agent to reduce or prevent negative withdrawal side effects associated with narcotic or alcohol withdrawal treatment.

24. The pharmaceutical composition of claim 23, wherein said anxiolytic agent comprises at least one member selected from the group consisting of a benzodiazepine, azaspirodecanedione, piperazine derivative, derivatives thereof, or pharmaceutically acceptable salts thereof.

25. The pharmaceutical composition of claim 24, wherein said benzodiazepine comprises at least one member selected from the group consisting of diazepam, alprazolam, clonazepam, clorazepate, chlordiazepoxide, halazepam, lorazepam, oxazepam, derivatives thereof, or pharmaceutically acceptable salts thereof.

26. The pharmaceutical composition of claim 25, wherein said benzodiazepine is chlordiazepoxide.

27. The pharmaceutical composition of claim 26, wherein said effective amount of said chlordiazepoxide is about 50–60 mg or less per dose.

28. The pharmaceutical composition of claim 25, wherein said benzodiazepine is lorazepam and said effective amount of said lorazepam is about 0.25–10 mg per dose.

29. The pharmaceutical composition of claim 23, wherein said centrally acting alpha antiadrenergic agent comprises of at least one member selected from the group consisting of methyldopa, clonidine, guanfacine, guanabenz, lofexidine, derivatives thereof and pharmaceutically acceptable salts thereof.

30. The pharmaceutical composition of claim 29, wherein said centrally acting alpha antiadrenergic agent is clonidine and said effective amount of said clonidine is about 0.05–0.7 mg per dose.

31. The pharmaceutical composition of claim 23, wherein said central nervous system stimulant agent comprises of at least one member selected from the group consisting of an amphetamine, methylphenidate, pemoline, caffeine, centrally acting alpha-1 agonist, derivatives thereof, and pharmaceutically acceptable salts thereof.

32. The pharmaceutical composition of claim 31, wherein said central nervous system stimulant is dextroamphetamine sulfate and said effective amount of said dextroamphetamine sulfate is about 1–20 mg per dose.

33. The pharmaceutical composition of claim 32, wherein said effective amount of said dextroamphetamine sulfate is in a sustained release form.

34. The pharmaceutical composition of claim 31, wherein said central nervous system stimulant agent is modafinil and said effective amount of said modafinil is about 50–400 mg or greater per dose.

35. The pharmaceutical composition of claim 34, wherein said effective amount of said modafinil is about 200 mg per dose.

36. The pharmaceutical composition of claim 35, wherein said composition comprises about 0.25–10 mg lorazepam, about 0.05–0.7 mg clonidine, and about 1–20 mg dextroamphetamine sulfate per dose of said combination.

37. The pharmaceutical composition of claim 36, wherein said combination comprises about 100 mg or less chlordiazepoxide, about 0.05–0.7 mg clonidine, and about 1–20 mg dextroamphetamine sulfate per dose of said combination.

38. The pharmaceutical composition of claim 36, wherein said combination comprises about 0.25–10 mg lorazepam, about 0.05–0.7 mg clonidine, and about 50–400 mg or greater of modafinil per dose of said combination.

39. The pharmaceutical composition of claim 36, wherein said combination comprises about 50–60 mg chlordiazepoxide, 0.05–0.7 mg clonidine, and about 50–400 mg or greater of modafinil per dose of said combination.

40. The pharmaceutical composition of claim 36, wherein said combination comprises about 0.25–10 mg of lorazepam, about 0.05–0.7 mg of clonidine, about 50–400 mg or greater of modafinil, and about 1–20 mg dextroamphetamine sulfate per dose of said combination.

42. The pharmaceutical composition of claim 36, wherein said combination comprises about 50–60 mg chlordiazepoxide, about 0.05–0.7 mg clonidine, about 1–20 mg of dextroamphetamine sulfate, and about 50–400 mg or greater modafinil per dose of said combination.

42. A pharmaceutical kit for treatment of narcotic withdrawal symptoms comprising the following three separate ingredients, combined in a kit:
   at least one anxiolytic agent;
   at least one centrally acting alpha antiadrenergic agent; and
   at least one central nervous system stimulant agent.

43. The pharmaceutical kit of claim 42, wherein said kit contains an effective amount of said anxiolytic agent to reduce anxiety and seizure, an effective amount of said centrally acting alpha antiadrenergic agent to reduce or prevent central and peripheral nerve agitation, and an effective amount of said central nervous system stimulant agent to reduce or prevent negative withdrawal side effects associated with narcotic withdrawal treatment.

44. The pharmaceutical kit of claim 43, wherein said anxiolytic agent comprises at least one member selected from the group consisting of a benzodiazepine, azaspirodecanedione, piperazine derivative, derivatives thereof, and pharmaceutically acceptable salts thereof.

45. The pharmaceutical kit of claim 44, wherein said benzodiazepine comprises at least one member selected from the group consisting of diazepam, alprazolam, clonazepam, clorazepate, chlordiazepoxide, halazopam, lorazepam, oxazepam, derivatives thereof, and pharmaceutically acceptable salts thereof.

46. The pharmaceutical kit of claim 44, wherein said benzodiazepine is lorazepam and said effective amount of said lorazepam is about 0.25–10 mg per dose.

47. The pharmaceutical kit of claim 43, wherein said centrally acting alpha antiadrenergic agent comprises of at least one member selected from the group consisting of methyldopa, clonidine, guanfacine, lofexidine, guanabenz, derivatives thereof and pharmaceutically acceptable salts thereof.

48. The pharmaceutical kit of claim,wherein said centrally acting alpha antiadrenergic agent is clonidine and said effective amount of said clonidine is about 0.05–0.7 mg per dose.

49. The pharmaceutical kit of claim 43, wherein said central nervous system stimulant agent comprises of at least one member selected from the group consisting of an amphetamine, methylphenidate, pemoline, caffeine, centrally acting alpha-1 agonist, derivatives thereof, and pharmaceutically acceptable salts thereof.

50. The pharmaceutical kit of claim 49, wherein said central nervous system stimulant agent is modafinil and said effective amount of said modafinil is about 50–400 mg or greater per dose.

51. The pharmaceutical kit of claim 50, wherein said effective amount of said modafinil is about 200 mg per dose.

52. The pharmaceutical kit of claim 43, wherein said anxiolytic agent comprises at least one member selected from the group consisting of a benzodiazepine, azaspirodecanedione, piperazine derivative, derivatives thereof, and pharmaceutically acceptable salts thereof; wherein said centrally acting alpha antiadrenergic agent comprises at least one member selected from the group consisting of methyl dopa, clonidine, guanfacine, lofexidine, guanabenz, derivatives thereof and pharmaceutically acceptable salts thereof; wherein said central nervous system stimulant agent comprises of at least one member selected from the group consisting of an amphetamine, methylphenidate, pemoline, caffeine,.centrally acting alpha-1 agonist,. derivatives thereof and pharmaceutically acceptable salts thereof; and further wherein said benzodiazepine comprises of at least one member selected from the group consisting of diazepam, alprazolam, clonazepam, chlorazepate, chlordiazepoxide, halazopam, lorazepam, oxazepam, derivatives thereof, and pharmaceutically acceptable salts thereof.

53. A pharmaceutical composition for the treatment of narcotic withdrawal symptoms comprising a combination of at least one anxiolytic agent; at least one centrally acting alpha antiadrenergic agent; and at least one central nervous system stimulant agent.

54. The pharmaceutical composition of claim 53, wherein said composition comprises of an effective amount of said anxiolytic agent to reduce anxiety and seizure, an effective amount of said centrally acting alpha antiadrenergic agent to reduce or prevent central and peripheral nerve agitation, and an effective amount of said central nervous system stimulant agent to reduce or prevent negative withdrawal side effects associated with narcotic withdrawal treatment.

55. The pharmaceutical composition of claim 54, wherein said anxiolytic agent comprises at least one member selected from the group consisting of a benzodiazepine, azaspirodecanedione, piperazine derivative, derivatives thereof, or pharmaceutically acceptable salts thereof.

56. The pharmaceutical composition of claim 55, wherein said benzodiazepine comprises at least one member selected from the group consisting of diazepam, alprazolam, clonazepam, clorazepate, chlordiazepoxide, halazopam, lorazepam, oxazepam, derivatives thereof, or pharmaceutically acceptable salts thereof.

57. The pharmaceutical composition of claim 56, wherein said benzodiazepine is lorazepam and said effective amount of said lorazepam is about 0.25–10 mg per dose.

58. The pharmaceutical composition of claim 54, wherein said centrally acting alpha antiadrenergic agent comprises of at least one member selected from the group consisting of methyldopa, clonidine, guanfacine, guanabenz, lofexidine, derivatives thereof and pharmaceutically acceptable salts thereof.

59. The pharmaceutical composition of claim 58, wherein said centrally acting alpha antiadrenergic agent is clonidine., and said effective amount of said clonidine is about 0.05–0.7 mg per dose.

60. The pharmaceutical composition of claim 54, wherein said central nervous system stimulant agent comprises of at least one member selected from the group consisting of an amphetamine, methylphenidate, pemoline, caffeine, centrally acting alpha-1 agonist, derivatives thereof, and pharmaceutically acceptable salts thereof.

61. The pharmaceutical composition of claim 60, wherein said central nervous system stimulant agent is modafinil and said effective amount of said modafinil is about 50–400 mg or greater per dose.

62. The pharmaceutical composition of claim 61, wherein said effective amount of said modafinil is about 200 mg per dose.

63. The pharmaceutical composition of claim 62, wherein said composition comprises about 0.25–10 mg lorazepam, about 0.05–0.7 mg clonidine, and about 1–20 mg dextroamphetamine sulfate per dose of said combination.

\* \* \* \* \*

UNITED STATES PATENT AND TRADEMARK OFFICE
CERTIFICATE OF CORRECTION

PATENT NO.    : 6,503,950 B1
DATED         : January 7, 2003
INVENTOR(S)   : David M. Ockert It is certified that error appears in the above-identified patent and that said Letters Patent is hereby corrected as shown below:

Column 1,
Line 31, after "detoxification" delete ".".

Column 11,
Line 43, after "claim" insert -- 47 --.

Column 12,
Line 4, after "caffeine," delete ".".
Line 5, after "agonist" delete ".".

Signed and Sealed this

Seventeenth Day of June, 2003

JAMES E. ROGAN
*Director of the United States Patent and Trademark Office*